(12) United States Patent
Li et al.

(10) Patent No.: US 8,927,684 B2
(45) Date of Patent: Jan. 6, 2015

(54) FLUORINATED MONOMERS, OLIGOMERS AND POLYMERS FOR USE IN ORGANIC ELECTRONIC DEVICES

(75) Inventors: Zhao Li, Orleans (CA); Jianfu Ding, Ottawa (CA); Jianping Lu, Orleans (CA); Ye Tao, Orleans (CA)

(73) Assignee: National Research Council of Canada, Ottawa, ON (CA)

( * ) Notice: Subject to any disclaimer, the term of this patent is extended or adjusted under 35 U.S.C. 154(b) by 285 days.

(21) Appl. No.: 13/510,736

(22) PCT Filed: Nov. 3, 2010

(86) PCT No.: PCT/CA2010/001732
§ 371 (c)(1),
(2), (4) Date: May 18, 2012

(87) PCT Pub. No.: WO2011/060526
PCT Pub. Date: May 26, 2011

(65) Prior Publication Data
US 2012/0232237 A1    Sep. 13, 2012

Related U.S. Application Data

(60) Provisional application No. 61/272,910, filed on Nov. 18, 2009.

(51) Int. Cl.
*C08G 73/06* (2006.01)
(Continued)

(52) U.S. Cl.
CPC ............. *H01L 51/0036* (2013.01); *B82Y 10/00* (2013.01); *C07D 285/10* (2013.01);
(Continued)

(58) Field of Classification Search
USPC ................................. 528/377, 423, 425, 401
See application file for complete search history.

(56) References Cited

U.S. PATENT DOCUMENTS

| 5,386,069 A | 1/1995 | Fauver et al. |
| 6,676,857 B2 | 1/2004 | Heeney et al. |
| 2004/0229925 A1 | 11/2004 | Zhang |

FOREIGN PATENT DOCUMENTS

| CA | 2625306 | 9/2009 |
| WO | 00/46321 | 8/2000 |

(Continued)

OTHER PUBLICATIONS

Babudri F, Farinola GM, Naso F, Ragni R. (2007) Chem. Commun. 1003-1022.

(Continued)

*Primary Examiner* — Duc Truong
(74) *Attorney, Agent, or Firm* — Catherine Lemay (57) ABSTRACT

Compounds of Formula (I): (formula (I)) where: $X_1$ and $X_2$ are the same or different and each is independently Cl, Br, I, a substituted or unsubstituted aryl group or a substituted or unsubstituted heteroaryl group; and, Y is O, S, Se, $NR_1$, $R_1C$—$CR_2$ or $R_1C$=$CR_2$, wherein $R_1$ and $R_2$ are the same or different and are each independently H or an organic group, are useful as monomers to produce oligomers or polymers that are useful in organic electronic devices.

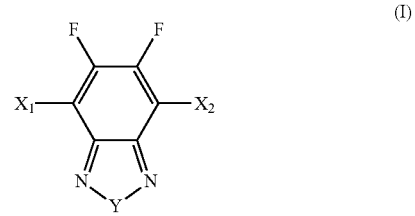

20 Claims, 2 Drawing Sheets (51) Int. Cl.
- *H01L 51/00* (2006.01)
- *B82Y 10/00* (2011.01)
- *C07D 285/10* (2006.01)
- *C07D 293/12* (2006.01)
- *C07D 417/14* (2006.01)
- *C07D 495/04* (2006.01)
- *C08G 61/12* (2006.01)
- *C08G 73/00* (2006.01)
- *H01L 51/42* (2006.01)

(52) U.S. Cl.
CPC ............ *C07D 293/12* (2013.01); *C07D 417/14* (2013.01); *C07D 495/04* (2013.01); *C08G 61/123* (2013.01); *C08G 61/126* (2013.01); *C08G 2261/3243* (2013.01); *C08G 2261/3246* (2013.01); *C08G 2261/3247* (2013.01); *H01L 51/0047* (2013.01); *H01L 51/4253* (2013.01); *Y02E 10/549* (2013.01)
USPC ............ 528/423; 528/377; 528/401; 528/425

(56) References Cited

FOREIGN PATENT DOCUMENTS

| WO | 02/059121 | 8/2002 |
|---|---|---|
| WO | 2006/010545 | 2/2006 |

OTHER PUBLICATIONS

ISR/WO PCT/CA2010/001732, National Research Council of Canada, Nov. 3, 2010.
Kitamura C, Tanaka S, Yamashita Y. (1996) Chem. Mater. 8, 570-578.
Lu J, Liang F, Drolet N, Ding J, Tao Y, Movileanua R. (2008) Chem. Commun. 5315-5317.
Price, S et al (2001) Fluorine Substituted Conjugated Polymer of Medium Band Gap Yields 7% Efficiency in Polymer-Fullerene Solar Cells. J. Am. Chem. Soc., 133, 4625-4631.
Uno T, Takagi K, Tomoeda M. (1980) Chem. Pharm. Bull. 28(6), 1909-1912.
Zhao, L et al (2011) Synthesis and applications of difluorobenzothiadiazole based conjugated polymers for organic photovoltaics. J. Mater. Chem., 21, 3226-3233.
Zhou, H (2011) Development of Fluorinated Benzothiadiazole as a Structural Unit for a Polymer Solar Cell of 7% Efficiency. Angew. Chem. Int. Ed., 50, 2995-2998.

FLUORINATED MONOMERS, OLIGOMERS AND POLYMERS FOR USE IN ORGANIC ELECTRONIC DEVICES

CROSS-REFERENCE TO RELATED APPLICATIONS

This application is a national phase entry of International Patent Application PCT/CA2010/001732 filed Nov. 3, 2010 and claims the benefit of U.S. Provisional patent application Ser. No. 61/272,910 filed Nov. 18, 2009, the entire contents of both of which are herein incorporated by reference.

FIELD OF THE INVENTION

The present invention relates to novel fluorinated monomers for producing novel fluorinated oligomers or polymers for use in organic electronic devices.

BACKGROUND OF THE INVENTION

Organic electronic devices have drawn a great deal of research interest in recent years because of their potential for broad commercial application, including electroluminescence devices, field effect transistors and organic solar cells, etc. In all these devices, the key component is organic semi-conducting materials, which are usually used as active thin layers. To get satisfactory device properties and performance, the chemical structures of these organic materials must be carefully controlled and optimized.

Among organic semiconductors, alternating conjugated polymers of an electron donor (ED) unit and an electron acceptor (EA) unit have attracted more and more attention due to their special properties associated with the donor/acceptor (D/A) structure in the main chain. This D/A structure can effectively lower the band gap of conjugated polymers, which is very important, especially for solar cell applications, where the polymer absorption should be fine-tuned to match the solar spectrum. Meanwhile, the energy offset between lowest unoccupied molecular orbital (LUMO) of the polymer and the fullerene derivatives (widely used electron acceptors in organic solar cells) should be well controlled to be just enough for charge separation in order to minimize energy loss. However, to fine tune the energy levels (HOMO, LUMO) of the conjugated polymer, and at the same time, optimize other properties, such as solid state packing, solubility, carrier mobility still tends to be difficult.

Fluorinated conjugated polymers show several advantages compared with non-fluorinated counterpart. First, they usually have lower HOMO and LUMO energy levels, which will increase open circuit voltage of photo voltaic devices and endow the polymer better resistance against the oxidation degradation process. Second, because of high electronegativity of fluorine, the resulting polymers can be used as n-type or ambipolar semiconducting materials. Third, sometimes, they can form C—H . . . F interactions, which can influence the solid state supramolecular organization, phase segregation and π-π stacking. This may enhance the charge carrier mobility. However, the number of fluorinated monomers with strong electron withdrawing ability is quite limited.

It is known that a monomer as illustrated in Scheme 1 is a strong electron acceptor unit exhibiting good properties in optoelectronic device applications (Zhang 2004).

Scheme 1

However, there are only a very limited number of methods to successfully introduce fluorine atoms on to an organic molecule. Two major methods have been reported to introduce fluorine atoms into an aromatic ring. The first, and most widely used method, uses the Balz-Schiemann Reaction. This approach involves conversion of aryl amines to aryl fluorides via diazotisation and subsequent thermal decomposition of the derived tetrafluoroborates or hexafluorophosphates. The second method uses butyl lithium and a special fluorinating agent, such as N-fluorobenzenesulfonimide. These two methods are usually tedious and involve multi-step synthesis. Very stringent reaction conditions are also usually involved which may not be compatible with many organic groups, especially with some groups having strong electron withdrawing properties, such as 2,1,3-benzothiadiazole. For these reasons, monomers containing fluorine and at the same time having strong electron withdrawing properties are quite limited in the art. One report describes fluorinated monomers and polymers containing 3-substituted-4-fluorothiophene units (Heeney 2004).

There remains a need for new monomers having improved electronic properties for use in producing new polymers for use in electronic devices.

SUMMARY OF THE INVENTION

There is provided a compound of Formula (I):

where: $X_1$ and $X_2$ are the same or different and each is independently Cl, Br, I, a substituted or unsubstituted aryl group or a substituted or unsubstituted heteroaryl group; and, Y is O, S, Se, $NR_1$, $R_1C$—$CR_2$ or $R_1C$=$CR_2$, wherein $R_1$ and $R_2$ are the same or different and are each independently H or an organic group.

There is further provided an oligomer or polymer comprising an electron-accepting monomer of Formula (I) copolymerized with an electron-donating co-monomer.

Compounds of Formula (I) are somewhat similar to compounds disclosed in U.S. patent publication 2004/0229925 (Zhang 2004), except two fluorine atoms have been introduced on to the aromatic ring. Introduction of the two fluorine atoms proved to be very difficult, with the preparation of compounds of Formula (I) not being readily achievable by usual methods. Further, the present difluoro-derivatives have even better properties than the non-fluorinated compounds of U.S. patent publication 2004/0229925. The presence of the two fluorine atoms further reduces the HOMO and LUMO energy levels of oligomers and polymers produced from the monomers. Thus, compared with the non-fluorinated counterpart, the present fluorinated oligomeric or polymeric materials have more finely-tuned band gaps and energy levels, enhanced π-stacking, higher carrier mobility, higher open circuit voltage ($V_{oc}$) for solar cell applications, greater resistance to oxidative degradation and better stability. Further, enhanced hydrophobicity and lipophilicity in perfluorinated substances leads to better phase separation, thus oligomers and polymers produced from the present monomers have a better solubility profile for enhanced crystallizing capability. Yet further, C—H . . . F interactions provide solid state supramolecular organization. The above properties are greatly desired for many applications in organic electronic devices.

Monomers of the present invention have improved electronic properties and are useful for producing polymers for use as active layers in organic electronic devices, for example optoelectronic devices, electroluminescence devices or field effect transistors. Such devices include, for example, optical sensors and photovoltaic devices (e.g. solar cells).

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

In compounds of Formula (I), $X_1$ and $X_2$ are the same or different and each is independently Cl, Br, I, a substituted or unsubstituted aryl group or a substituted or unsubstituted heteroaryl group; and, Y is O, S, Se, $NR_1$, $R_1C$—$CR_2$ or $R_1C$=$CR_2$, wherein $R_1$ and $R_2$ are the same or different and are each independently H or an organic group.

Aryl groups are preferably $C_6$-$C_{18}$-aryl groups, for example, phenyl, naphthyl or anthracyl. Heteroaryl groups contain one or more heteroatoms, for example, N, O or S, in the ring. Heteroaryl groups are preferably $C_3$-$C_{14}$-heteroaryl groups. Preferably, heteroaryl groups contain 1, 2 or 3 heteroatoms in the ring, more preferably 1 or 2 heteroatoms, yet more preferably 1 heteroatom. Preferably, the heteroatom is N or S, more preferably S. Some examples of heteroaryl groups include pyridinyl, pyridazinyl, pyrimidyl, pyrazyl, triazinyl, pyrrolyl, pyrazolyl, imidazolyl, (1,2,3,)-triazolyl, (1,2,4)-triazolyl, pyrazinyl, pyrimidinyl, tetrazolyl, furyl, thienyl, isoxazolyl, thiazolyl, isoxazolyl, oxazolyl, benzofuranyl, benzothiophenyl, indolyl, 1H-indazolyl, indolinyl, benzopyrazolyl, 1,3-benzodioxolyl, benzoxazolyl, purinyl, tetralinyl, coumarinyl, chromonyl, quinolinyl, isoquinolinyl, benzimidazolyl, quinazolinyl, pyrido[2,3-b]pyrazinyl, pyrido[3,2-c]pyridazinyl, pyrido[3,4-b]-pyridinyl, 2(1H)-quinolonyl, 1(2H)-isoquinolonyl, 1,4-benzisoxazinyl, naphthyridinyl, benzothiazolyl, quinoxalinyl, benzoxazinyl, phthalazinyl and cinnolinyl. The aryl or heteroaryl group is preferably phenyl or thienyl, more preferably thienyl.

Aryl or heteroaryl groups may be unsubstituted or substituted. Substituents may be any suitable moiety, for example, one or more of halo (e.g. F, Cl, Br, I), hydroxy, oxo, amino, amido, carboxy, nitro, thio, $C_1$-$C_{20}$-alkyl, $C_2$-$C_{20}$-alkenyl, $C_2$-$C_{20}$-alkynyl, $C_6$-$C_{20}$-aryl, $C_7$-$C_{24}$-alkaryl, $C_1$-$C_{20}$-alkoxy, $C_2$-$C_{20}$-alkenoxy, $C_2$-$C_{20}$-alkynoxy, $C_6$-$C_{20}$-aryloxy, $C_1$-$C_{20}$-alkylamino, $C_2$-$C_{40}$-dialkylamino, $C_1$-$C_{20}$-alkamido, $C_2$-$C_{20}$-carboxy or $C_1$-$C_{20}$-carbonyl. Preferably, the substituent is one or more of Cl, Br or $C_1$-$C_{20}$-alkyl. The substituents may in turn be substituted by other subsituents defined in the above list.

$R_1$ and $R_2$ are preferably independently H, $C_1$-$C_{20}$-alkyl, $C_2$-$C_{20}$-alkenyl, $C_2$-$C_{20}$-alkynyl, $C_6$-$C_{20}$-aryl, $C_7$-$C_{24}$-alkaryl, $C_1$-$C_{20}$-alkoxy, $C_2$-$C_{20}$-alkenoxy, $C_2$-$C_{20}$-alkynoxy, $C_6$-$C_{20}$-aryloxy, $C_1$-$C_{20}$-alkylamino, $C_2$-$C_{40}$-dialkylamino, $C_1$-$C_{20}$-alkamido, $C_2$-$C_{20}$-carboxy or $C_1$-$C_{20}$-carbonyl, or $R_1$ and/or $R_2$ taken together with Y form a $C_6$-$C_{20}$-carbocyclic or $C_3$-$C_{24}$-heterocyclic group. Carbocyclic and heterocyclic groups may be, for example, aryl and heteroaryl groups as previously defined. $R_1$ and $R_2$ may or may not be substituted by one or more of the substituents listed previously in connection with the aryl and heteroaryl groups defined for $X_1$ and $X_2$.

Preferably, $X_1$ and $X_2$ are Br, thienyl, brominated thienyl, $C_1$-$C_{20}$-alkyl substituted thienyl or $C_1$-$C_{20}$-alkyl substituted brominated thienyl. Preferably, $X_1$ and $X_2$ are the same. Y is preferably S or Se, more preferably S.

Synthesis of Monomers

Compounds of Formula (I) may be prepared as shown in Scheme 2.

In Scheme 2, 1,4-disubstituted-2,3-difluorobenzene is used as a starting material, which can be prepared by generally known methods from o-difluorobenzene (Dunn 2006). Nitration of 1,4-disubstituted-2,3-difluorobenzene introduces two nitro groups in the 5- and 6-positions of the benzene ring. Nitration may be achieved by generally known methods, such as the one described by Uno et al. (Uno 1980). The two nitro groups are then reduced to two amino groups which can react with other compound to form fused ring structure. Reduction of the nitro groups to amino groups may be accomplished by generally known methods (Kitamura 1996), for example with reducing metals such as iron under acidic conditions. Ring closure may be accomplished by generally known reactions in which the amino hydrogen atoms combine with leaving groups in compounds that comprise the Y moiety (Kitamura 1996).

Alternatively, compounds of Formula (I) may be prepared as shown in Scheme 3.

and longer reaction time. After separation of the di-nitrated compound, the bromine atoms of the di-nitrated compound can be converted to $X_1$ and $X_2$ groups by an appropriate coupling reaction, e.g. a Stille reaction. Then, the nitro groups may be reduced to amine groups in the same manner as in Scheme 2. Ring closure may then be accomplished in the same manner as in Scheme 2. The $X_1$ and $X_2$ groups may be converted to other $X_1$ and $X_2$ groups by suitable reactions generally known in the art. For example, halogenation, such as bromination, may be effected in order to provide $X_1$ and $X_2$ groups comprising halogen groups to assist in further polymerization of the monomer.

Synthesis of Oligomers and Polymers

Compounds of Formula (I) may be used as monomers to produce fluorinated conjugated oligomers or polymers by generally known methods, for example, by Suzuki coupling In Scheme 3, 2,3-difluoro-1,4-dibromobenzene is nitrated in the same manner as in Scheme 2. This affords a mixture of mono-, di- and tri-nitrated material. A tri-nitrated compound is formed because one of the bromine atoms will also be substituted by a nitro group at higher reaction temperature or Stille coupling (Lu 2008). Compounds of Formula (I) have very strong electron-accepting properties and are generally copolymerized with one or more co-monomers having electron-donating properties. Exemplary groups of co-monomers having electron-donating properties include substituted or unsubstituted phenyls, thienes, fluorenes, carbazoles, benzodithiophenes, pyrroles, indenofluorenes, indolocarbazoles, dibenzosiloles, dithienosiloles, benzo[1,2-b;3,4-b]dithiophenes, benzo[2,1-b:3,4-b']dithiophenes, cyclopenta[2,1-b:3,4-b]dithiophenes, thieno[3,2-b]thiophenes, thieno[3,4-b]thiophenes and dithieno[3,2-b:2',3'-d]pyrroles, where any substituents may be one or more of $X_1$ or $X_2$ as defined previously. Specific examples of co-monomers having electron-donating properties include 2,7-bis(4,4,5,5,-tetramethyl-1,3,2-dioxaborolan-2-yl)-9,9-di(2-ethylhexyl)-fluorene, fluorene, carbazole and benzodithiophene.

Further, in addition to being copolymerized with one or more electron-donating monomers, compounds of Formula (I) may also be copolymerized with one or more other electron-accepting monomers to produce oligomers or polymers comprising two or more different electron-accepting monomers and one or more different electron-donating monomers. Some examples of other electron-accepting monomers include substituted or unsubstituted benzothiadiazole, thienopyrazine, quinoxaline, dihydropyrrolo[3,4-]pyrrole-1,4-dione, thieno[3,4-b]thiophene, where any substituents may be one or more of $X_1$ or $X_2$ as defined previously.

Electron-accepting monomers may be copolymerized with electron-donating monomers in various ratios to tune the electronic properties of the resulting oligomer or polymer. The ratio of electron-accepting monomer to electron-donating monomer may be in a range of from 1:99 to 99:1 mol %, preferably 40:60 to 60:40 mol %. In oligomers or polymers where other electron-accepting monomers are present, the ratio of monomers from compounds of Formula (I) to the other electron-accepting monomers is preferably 99:1 to 10:90 mol %.

Oligomers and polymers of the present invention preferably have from 2 to 20,000 monomeric units, more preferably from 10 to 10,000 monomeric units.

Oligomers and polymers of the present invention may be cast as thin films or membranes by methods generally known in the art, for example, spin-coating, casting or printing, and ultimately assembled into organic electronic devices.

Example 1

Synthesis of Fluorinated Monomer (Monomer 2)

Step 1: Synthesis of
2,3-difluoro-1,4-dibromo-5,6-dinitro-benzene 2,3-difluoro-1,4-dibromo-benzene as the starting raw material was synthesized according to prior methods (Dunn 2006). In a 250 ml flask, concentrated sulphuric acid (50 ml) was added and cooled to 0-5° C. in an ice water bath. Fuming nitric acid (50 ml) and 2,3-difluoro-1,4-dibromo-benzene (10 g, 36.8 mmol) were slowly added. Then, the flask was heated to 65° C. for 14 h. The mixture was then precipitated into ice water. The resulting yellow solid was filtered and purified by column chromatograph with a mixture of hexane and dichloromethane (1:4 v/v) to afford 2,3-difluoro-1,4-dibromo-5,6-dinitro-benzene (3.5 g, 26%). $^1$H and $^{19}$F NMR spectra were as expected.

Step 2: Synthesis of
2,3-difluoro-1,4-di(2-thienyl)-5,6-dinitro-benzene 2,3-difluoro-1,4-dibromo-5,6-dinitro-benzene (3.62 g, 10.0 mmol), 2-tributyl stannyl-thiophene (8.21 g, 22.0 mmol) and dichlorobis(triphenylphosphine) palladium (0.28 g, 0.40 mmol) were added into a 250 ml flask fitted with a condenser. After degassing and purging with Ar three times, 100 ml dry tetrahydrofuran (THF) was added. Then the mixture heated to reflux under Ar for 54 h. THF was removed by evaporation and the remaining solid was purified by column chromatograph to afford 2,3-difluoro-1,4-di(2-thienyl)-5,6-dinitro-benzene as yellow powder (3.0 g, 82%). $^1$H and $^{19}$F NMR spectra were as expected.

Step 3: Synthesis of
2,3-difluoro-1,4-di(2-thienyl)-5,6-diamino-benzene 2,3-difluoro-1,4-di(2-thienyl)-5,6-dinitro-benzene (3.0 g, 8.15 mmol), iron powder (5.5 g, 98 mmol) and acetic acid (100 ml) were stirred at 45° C. for 4 h. Then the mixture was poured into cold 5% NaOH solution (250 ml) and extracted with diethyl ether three times. The ether phase was washed with $NaHCO_3$ solution, dried over $MgSO_4$ and concentrated. Purification with column chromatograph afforded 2,3-difluoro-1,4-di(2-thienyl)-5,6-diamino-benzene as yellow powder (2.1 g, 84%). $^1$H and $^{19}$F NMR spectra were as expected.

Step 4: Synthesis of 5,6-difluoro-4,7-di(2-thienyl)-2,1,3-benzothiadiazole 2,3-difluoro-1,4-di(2-thienyl)-5,6-diamino-benzene (1.2 g, 3.9 mmol) was added into a small flask and purged with Ar three times. Then, dry pyridine (24 ml), N-thionylaniline (1.08 g, 7.8 mmol) and chlorotrimethylsilane (0.76 g, 7.0 mmol) were added. The mixture was stirred at 80° C. for 16 h before poured into ice water. The yellow precipitate was then filtered and washed with a mixture of ethanol and water (1:1 v/v) to afford 5,6-difluoro-4,7-di(2-thienyl)-2,1,3-benzothiadiazole as a yellow solid (1.3 g, 98%). $^1$H and $^{19}$F NMR spectra were as expected.

Step 5: Synthesis of 5,6-difluoro-4,7-di(5-bromo-2-thienyl)-2,1,3-benzothiadiazole 5,6-difluoro-4,7-di(2-thienyl)-2,1,3-benzothiadiazole (1.07 g, 3.18 mmol), N-bromosuccinimide (1.132 g, 6.36 mmol) and o-dichloroenzene (20 ml) were stirred at 55° C. for 3 h. Then o-dichlorobenzene was removed by vacuum distillation and the remaining solid was washed with ethanol and water before further purification by recrystallization from toluene (45 ml) to afford yellow crystals of 5,6-difluoro-4,7-di(5-bromo-2-thienyl)-2,1,3-benzothiadiazole (Monomer 2) (1.32 g, 84%). $^1$H and $^{19}$F NMR spectra were as expected.

Example 2

Synthesis of Other Monomers

In a manner similar to the synthesis of Monomer 2 in Example 1, four other monomers were synthesized. Table 1 lists five examples of monomers that were synthesized in this manner.

TABLE 1

| Compound | Structure |
|---|---|
| Monomer 1 | [structure: 5,6-difluoro-4,7-dibromo-2,1,3-benzothiadiazole] |
| Monomer 2 | [structure: 5,6-difluoro-4,7-bis(5-bromothien-2-yl)-2,1,3-benzothiadiazole] |
| Monomer 3 | [structure: 5,6-difluoro-4,7-bis(5'-bromo-3'-octylthien-2-yl)-2,1,3-benzothiadiazole] |
| Monomer 4 | [structure: 5,6-difluoro-4,7-bis(5-bromothien-2-yl)-2,1,3-benzoselenadiazole] |
| Monomer 5 | [structure: 5,6-difluoro-4,7-bis(5'-bromo-3'-octylthien-2-yl)-2,1,3-benzoselenadiazole] |

Example 3

Synthesis of Fluorinated Conjugated Polymer BDT-FBT from Monomer 3

Carefully purified 2,6-bis(trimethyltin)-4,8-bis(3-pentyl undecyl)benzo[1,2-b:4,5-b']dithiophene (0.289 g, 0.300 mmol), 5,6-difluoro-4,7-bis(5'-bromo-3',4'-dioctyl-2,2'bithiophen-5-yl)-2,1,3-benzothiadiazole (0.205 g, 0.300 mmol) were added in a small flask and purged with Ar several times. Then (PPh$_3$)$_4$Pd(0) (1 mol %) was added in a dry box. Toluene (8 ml) was added. The mixture was stirred and refluxed for 24 h before being poured into methanol. The resulting fibre-like polymer (BDT-FBT) was filtered and washed with hexane and acetone to afford a red solid (0.20 g, 57%). $^1$H and $^{19}$F NMR spectra were as expected. A non-fluorinated polymer (BDT-BT) was synthesized in a similar manner except that a non-fluorinated monomer was used (Lu 2008). The structures of BDT-FBT and BDT-BT are shown in Scheme 4.

Scheme 4

BDT-FBT

BDT-BT

Example 4

Characterization of BDT-FBT Polymer

BDT-FBT and BDT-BT were characterized by solubility, differential scanning calorimetry (DSC), ultraviolet (UV) spectroscopy and cyclic voltammetry (CV). Thin film transistors (TFT) based on these two polymers were fabricated and their performance was compared.

Non-fluorinated polymer BDT-BT shows some solubility in dicholorbenzene (DCB) at ambient temperature while fluorinated polymer BDT-FBT can only dissolve in DCB at a temperature above 60° C. Both polymers show similar UV absorption spectra in solution and as a film.

Figure 1:
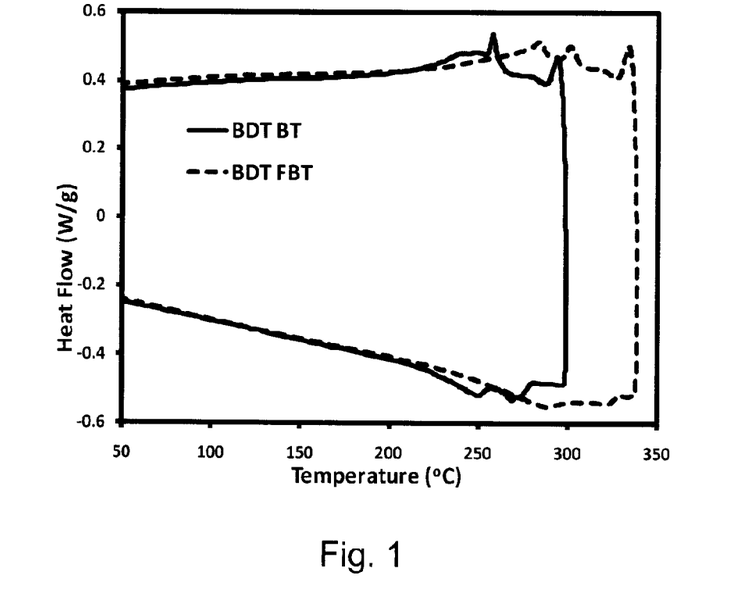
FIG. 1 depicts differential scanning calorimetry (DSC) curves of BDT-FBT and BDT-BT.

With reference to FIG. 1, differential scanning calorimetry (DSC) shows that BDT-FBT has a melting peak at a higher temperature (about 340° C.) than BDT-BT (about 300° C.) indicating higher crystallization capability for BDT-FBT over the non-fluorinated counterpart. Differential scanning calorimetry (DSC) analysis was carried out on a TA Instruments DSC 2920 under nitrogen at a heating/cooling rate of 10° C./min.

Figure 2:
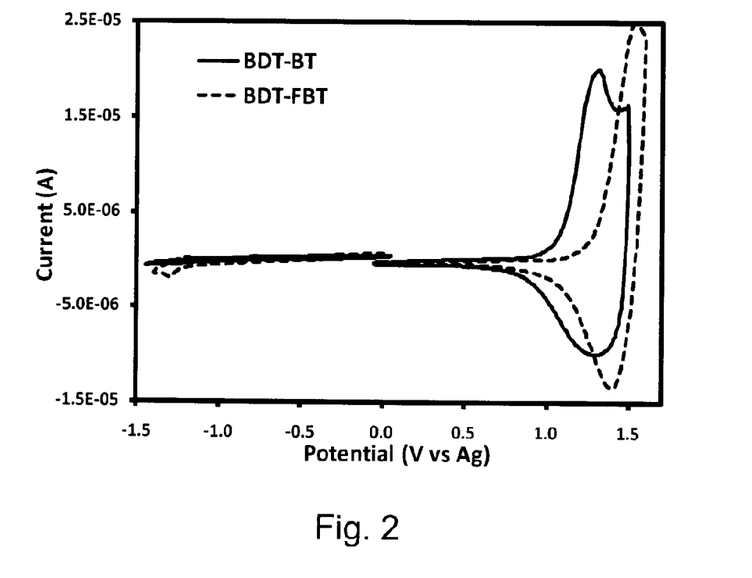
FIG. 2 depicts cyclic voltammetry (CV) curves of BDT-FBT and BDT-BT.

With reference to FIG. 2, cyclic voltammetry (CV) on BDT-FBT and BDT-BT shows that BDT-FBT has greater oxidative stability than the non-fluorinated counterpart. The CV results indicate that BDT-FBT has a lower HOMO and LUMO than BDT-BT by about 0.15 eV. The cyclic voltammetry measurements were carried out in a three-electrode cell under argon using silver electrode and 0.1 M Bu$_4$NPF$_6$ salt in anhydrous CH$_3$CN as the supporting electrolyte.

Bottom-contact thin film transistors were fabricated by spin-coating BDT-BT and BDT-FBT solution at 60° C. on heavily doped n-Si wafers with an overlayer of SiO$_2$ (230 nm, $C_i=15$ nF/cm$^2$). Then gold source and drain electrodes were sputtered on top of polymers. The transistor channel length and width are 20 μm and 10 mm, respectively. The current-voltage (JV) characteristics were measured with a computer-controlled semiconductor parameter analyzer (HP4145A) in a N$_2$ glove box. The hole mobility was deduced from the saturation regime of the JV characteristics. Hole mobilities in the TFTs were found to be BDT-BT=2.12×10$^{-4}$ cm$^2$/Vs and BDT-FBT=4.88×10$^{-5}$ cm$^2$/Vs.

Example 5

Fabrication of a Solar Cell from BDT-FBT Polymer

Polymer solar cells were fabricated with a general structure of ITO/PEDOT-PSS/Polymer:PC$_{71}$BM/LiF/Al. Patterned indium tin oxide (ITO) glass substrates were cleaned with detergent before sonication in CMOS grade acetone and isopropanol for 15 min. The organic residue was further removed from the substrates by treating with UV-ozone for 10 min. Then a thin layer of PEDOT:PSS (Clevios P, H. C. Starck, 45 nm) was spin-coated and dried for 1 h at 120° C. BDT-FBT polymer and PC$_{71}$BM (ADS) (1:2 weight ratio) was dissolved in 1,2,4-trichlorobenzene at 80° C. The solution was filtered and spin-coated on the top of the PEDOT: PSS layer. The border of the PEDOT:PSS layer and active layer was mechanically removed before 1.0 nm of LiF and 100 nm Al layers were created by thermal evaporation through a shadow mask at a pressure of 5×10$^{-7}$ mbar in a Boc Edwards Auto 500 System.

Figure 3:
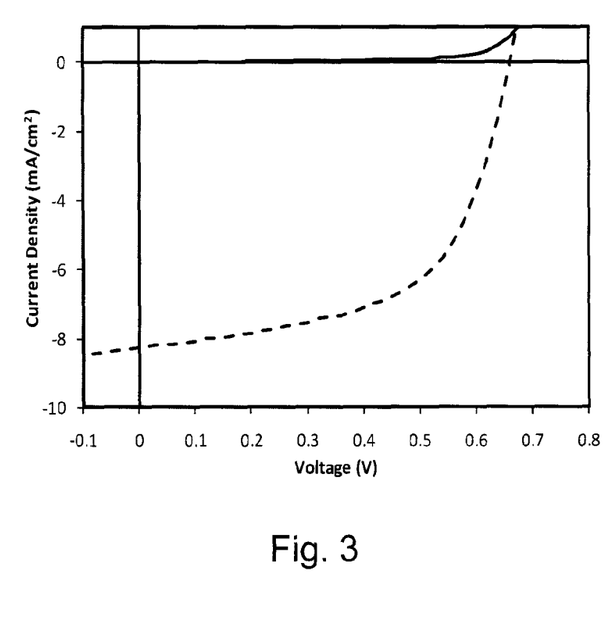
FIG. 3 depicts a typical J-V curve of BDT-FBT polymer: $PC_{71}BM$ based solar cell device under illumination of AM 1.5G, 100 mW/cm².

Current density-voltage (J-V) characteristics of the devices were measured with a Keithley 2400 digital source meter under simulated air mass (AM) 1.5 solar irradiation of 100 mW/cm$^2$ (Sciencetech Inc., SF150). FIG. 3 depicts a typical J-V curve showing a $V_{oc}$ of 0.67 V, a short-circuit current density ($J_{sc}$) of 8.3 mNcm$^2$ and a fill factor (FF) of 0.57. Power conversion efficiency (PCE) thus reached 3.2%.

REFERENCES

The contents of the entirety of each of which are incorporated by this reference.

Babudri F, Farinola G M, Naso F, Ragni R. (2007) *Chem. Commun.* 1003-1022.
Burroughes J, Towns C, Pounds T, Halls J. (2002) International patent publication WO 02/059121 published Aug. 1, 2002.
Dunn J, Elworthy T R, Stefanidis D, Sweenet Z K. (2006) International patent publication WO 2006/010545 published Feb. 2, 2006.
Fauver J S, Fagerburg D R. (1995) U.S. Pat. No. 5,386,069 issued Jan. 31, 1995.
Heeney M, Farrand L, Giles M, Thompson M, Tierney S, Shkunov M, Sparrowe D, McCulloch I. (2004) U.S. Pat. No. 6,676,857 issued Jan. 13, 2004.
Inbasekaran M, Woo E P, Wu W, Bernius M T. (2000) International patent publication WO 00/46321 published Aug. 10, 2000.
Kitamura C, Tanaka S, Yamashita Y. (1996) *Chem. Mater.* 8, 570-578.
Lu J, Liang F, Drolet N, Ding J, Tao Y, Movileanua R. (2008) *Chem. Commun.* 5315-5317.
Uno T, Takagi K, Tomoeda M. (1980) *Chem. Pharm. Bull.* 28(6), 1909-1912.
Zhang C. (2004) U.S. patent publication 2004/0229925 published Nov. 18, 2004.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

What is claimed is:

1. A compound of Formula (I):

where: $X_1$ and $X_2$ are the same or different and each is independently Cl, Br, I, a substituted or unsubstituted aryl group or a substituted or unsubstituted heteroaryl group; and, Y is O, S, Se, NR$_1$, R$_1$C—CR$_2$ or R$_1$C=CR$_2$, wherein R$_1$ and R$_2$ are the same or different and are each independently H or an organic group.

2. The compound according to claim 1, wherein the aryl groups are C$_6$-C$_{18}$-aryl groups and the heteroaryl groups are C$_3$-C$_{14}$-heteroaryl groups having one or more of N, O or S in the ring.

3. The compound according to claim 1, wherein substituents on the aryl or heteroaryl group are one or more of halo, hydroxy, oxo, amino, amido, carboxy, nitro, thio, C$_1$-C$_{20}$-alkyl, C$_2$-C$_{20}$-alkenyl, C$_2$-C$_{20}$-alkynyl, C$_6$-C$_{20}$-aryl, C$_7$-C$_{24}$-alkaryl, C$_1$-C$_{20}$-alkoxy, C$_2$-C$_{20}$-alkenoxy, C$_2$-C$_{20}$-alkynoxy, C$_6$-C$_{20}$-aryloxy, C$_1$-C$_{20}$-alkylamino, C$_2$-C$_{40}$-dialkylamino, C$_1$-C$_{20}$-alkamido, C$_2$-C$_{20}$-carboxy or C$_1$-C$_{20}$-carbonyl.

4. The compound according to claim 1, wherein the aryl groups are phenyl, naphthyl or anthracyl and the heteroaryl groups are pyridinyl, pyridazinyl, pyrimidyl, pyrazyl, triazinyl, pyrrolyl, pyrazolyl, imidazolyl, (1,2,3,)-triazolyl, (1,2,4)-triazolyl, pyrazinyl, pyrimidinyl, tetrazolyl, furyl, thienyl, isoxazolyl, thiazolyl, isoxazolyl, oxazolyl, benzofuranyl, benzothiophenyl, indolyl, 1H-indazolyl, indolinyl, benzopyrazolyl, 1,3-benzodioxolyl, benzoxazolyl, purinyl, tetralinyl, coumarinyl, chromonyl, quinolinyl, isoquinolinyl, benzimidazolyl, quinazolinyl, pyrido[2,3-b]pyrazinyl, pyrido[3,2-c]pyridazinyl, pyrido[3,4-b]-pyridinyl, 2(1H)-quinolonyl, 1(2H)-isoquinolonyl, 1,4-benzisoxazinyl, naphthyridinyl, benzothiazolyl, quinoxalinyl, benzoxazinyl, phthalazinyl or cinnolinyl.

5. The compound according to claim 1, wherein $X_1$ and $X_2$ are the same or different and each is independently Br, thienyl, brominated thienyl, C$_1$-C$_{20}$-alkyl substituted thienyl or C$_1$-C$_{20}$-alkyl substituted brominated thienyl.

6. The compound according to claim 1, wherein $X_1$ and $X_2$ are the same and are Br, brominated thienyl or octyl substituted brominated thienyl.

7. The compound according to claim 1, wherein R$_1$ and R$_2$ are independently H, C$_1$-C$_{20}$-alkyl, C$_2$-C$_{20}$-alkenyl, C$_2$-C$_{20}$-alkynyl, C$_6$-C$_{20}$-aryl, C$_7$-C$_{24}$-alkaryl, C$_1$-C$_{20}$-alkoxy, C$_2$-C$_{20}$-alkenoxy, C$_2$-C$_{20}$-alkynoxy, C$_6$-C$_{20}$-aryloxy, C$_1$-C$_{20}$-alkylamino, C$_2$-C$_{40}$-dialkylamino, C$_1$-C$_{20}$-alkamido, C$_2$-C$_{20}$-carboxy or C$_1$-C$_{20}$-carbonyl, or R$_1$ and/or R$_2$ taken together with Y form a C$_6$-C$_{20}$-carbocyclic or C$_3$-C$_{24}$-heterocyclic group.

8. The compound according to claim 1, wherein Y is S.

9. The compound according to claim 1, wherein Y is Se.

10. An oligomer or polymer comprising an electron-accepting monomer of Formula (I) as defined in claim 1 copolymerized with an electron-donating co-monomer.

11. The oligomer or polymer according to claim 10, wherein the electron-donating co-monomer is one or more of a substituted or unsubstituted phenyl, thiene, fluorene, carbazole, benzodithiophene, pyrrole, indenofluorene, indolocarbazole, dibenzosilole, dithienosilole, benzo[1,2-b;3,4-b]dithiophene, benzo[2,1-b:3,4-b']dithiophene, cyclopenta[2,1-b:3,4-b']dithiophene, thieno[3,2-b]thiophene, thieno[3,4-b]thiophene or dithieno[3,2-b:2',3'-d]pyrrole, where the substituent, if present, is one or more of Cl, Br, I, a $C_6$-$C_{18}$-aryl group or a $C_3$-$C_{14}$-heteroaryl group having one or more of N, O or S in the ring.

12. The oligomer or polymer according to claim 10, wherein the electron-donating co-monomer is fluorene, carbazole or benzodithiophene.

13. The oligomer or polymer according to claim 10, further comprising one or more electron-accepting monomers other than the monomer of Formula (I).

14. The oligomer or polymer according to claim 13, wherein the one or more electron-accepting monomers other than the monomer of Formula (I) is a substituted or unsubstituted benzothiadiazole, thienopyrazine, quinoxaline, dihydropyrrolo[3,4-]pyrrole-1,4-dione, thieno[3,4-b]thiophene, where the substituent, if present, is one or more of Cl, Br, I, a $C_6$-$C_{18}$-aryl group or a $C_3$-$C_{14}$-heteroaryl group having one or more of N, O or S in the ring.

15. The oligomer or polymer according to claim 10 having a ratio of electron-accepting monomer to electron-donating co-monomer in a range of from 1:99 to 99:1 mol %.

16. The oligomer or polymer according to claim 10 having a ratio of electron-accepting monomer to electron-donating co-monomer in a range of from 40:60 to 60:40 mol %.

17. The oligomer or polymer according to claim 10, comprising from 2 to 20,000 monomeric units.

18. The oligomer or polymer according to claim 10, comprising from 10 to 10,000 monomeric units.

19. A film or membrane comprising the oligomer or polymer as defined in claim 10.

20. A process for producing a compound of Formula (I) as defined in claim 1 comprising:

* * * * *